United States Patent
Brunet et al.

[11] 3,975,437
[45] Aug. 17, 1976

[54] DIBENZO [a,d] CYCLOHEPTENE DERIVATIVES

[75] Inventors: Jean-Paul Brunet, Creteil; André Cometti, Paris, both of France

[73] Assignee: Rhone-Poulenc S.A., Paris, France

[22] Filed: Mar. 7, 1975

[21] Appl. No.: 556,389

Related U.S. Application Data
[62] Division of Ser. No. 447,059, Feb. 28, 1974, Pat. No. 3,933,905.

[30] Foreign Application Priority Data
Mar. 2, 1973   France .............................. 73.07508
Oct. 19, 1973   France .............................. 73.17404
Jan. 23, 1974   France .............................. 74.02214

[52] U.S. Cl. .............. 260/558 P; 260/247.1 R;
260/247.5 R; 260/268 TR; 260/293.56;
260/326.82; 260/326.87; 260/340.9; 260/465
R; 260/465 F; 260/465 G; 260/469; 260/470;
260/473 F; 260/515 R; 260/515 A; 260/516;
260/544 C; 260/557 B; 260/558 R; 260/558
D; 260/558.5; 260/559 R; 424/324
[51] Int. Cl.² ............. C07C 103/20; C07C 103/76
[58] Field of Search... 260/557 B, 558 R, 570.8 TC,
260/517, 518 R, 558 P, 518 A

[56] References Cited
UNITED STATES PATENTS
3,754,021   8/1973   Shen et al. .................. 260/518 R X
3,829,467   8/1974   Diamond et al. ............ 260/518 A X
3,856,857   12/1974   Beregi et al. ................ 260/518 R X
3,868,414   2/1975   Shen et al. .................. 260/518 R X OTHER PUBLICATIONS
"Tricyclic Compounds", Allais et al., CA78: 111018s (1973).

"Tricyclic Imines", Dostert et al., CA77: 19451j (1972).

*Primary Examiner*—Robert V. Hines
*Assistant Examiner*—Thomas A. Waltz
*Attorney, Agent, or Firm*—Stevens, Davis, Miller & Mosher

[57] ABSTRACT

Dibenzo[a,d]cycloheptene derivatives of the formula:

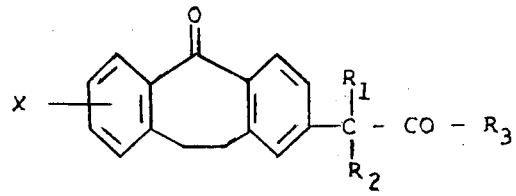

wherein x represents hydrogen, halogen, alkyl, alkoxy, alkylthio or trifluoromethyl, $R_1$ and $R_2$ represent hydrogen or alkyl, and $R_3$ represents hydroxy, alkoxy, 4-(2,4-dimethyl-1,3-dioxolanyl)-methoxy, or a group —$NR_4R_5$ in which $R_4$ and $R_5$ represents hydrogen, alkyl, hydroxyalkyl or phenyl, or —$NR_4R_5$ represents a mononuclear 5- or 6-membered heterocyclic group containing a second hetero atom selected from oxygen, sulphur, and nitrogen which is optionally substituted by alkyl, said alkyl, alkoxy, alkylthio and hydroxyalkyl radicals containing 1 to 4 carbon atoms, are new compounds possessing pharmacological properties, more particularly analgesic, antipyretic and anti-inflammatory properties.

5 Claims, No Drawings

DIBENZO (a,d) CYCLOHEPTENE DERIVATIVES

This is a division of application Ser. No. 447,059, filed Feb. 28, 1974, now U.S. Pat. No. 3,933,905.

This invention relates to new therapeutically useful dibenzo[a,d]cycloheptene derivatives, to processes for their preparation and to pharmaceutical compositions containing them.

The dibenzo[a,d]cycloheptene derivatives of the present invention are those compounds of the general formula:

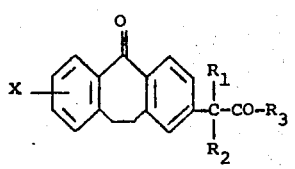
I wherein X represents a hydrogen or halogen atom, or an alkyl, alkoxy or alkylthio radical, each such radical containing 1 to 4 carbon atoms, or the trifluoromethyl radical, $R_1$ and $R_2$, which may have the same or different significances, each represent a hydrogen atom or an alkyl radical containing 1 to 4 carbon atoms, and $R_3$ represents a hydroxy radical, an alkoxy radical containing 1 to 4 carbon atoms, a 4-(2,2-dimethyl-1,3-dioxolanyl)-methoxy radical, or a group —$NR_4R_5$ in which $R_4$ and $R_5$, which may have the same or different significances, each represent a hydrogen atom, or an alkyl or hydroxyalkyl radical, each such radical containing 1 to 4 carbon atoms, or a phenyl radical, or $R_4$ and $R_5$, together with the nitrogen atom to which they are attached, represent a mononuclear 5- or 6-membered heterocyclic group optionally containing a second hetero atom selected from oxygen, sulphur, and nitrogen which is optionally substituted by an alkyl radical containing 1 to 4 carbon atoms (for example pyrrolid-1-yl, piperidino, morpholino, piperazin-1-yl and 4-methyl-piperazin-1-yl), and salts thereof.

According to a feature of the invention, the compounds of general formula I, wherein $R_3$ represents a group —$NR_4R_5$ in which $R_4$ and $R_5$ both represent hydrogen atoms, are prepared by the process which comprises the cyclisation and partial hydrolysis of a compound of the general formula:

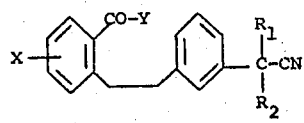
II wherein X, $R_1$ and $R_2$ are as hereinbefore defined and Y represents a hydroxy radical or a chlorine atom.

When in general formula II Y represents a hydroxy radical, the cyclisation and the partial hydrolysis can be carried out simultaneously to give a dibenzo[a,d]cycloheptene derivative of the general formula:

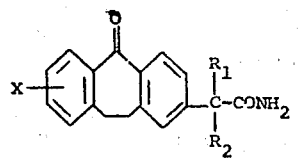
III wherein X, $R_1$ and $R_2$ are as hereinbefore defined. The reaction is generally carried out by heating the compound of general formula II (Y=OH) in polyphosphoric acid, preferably at a temperature of about 100°C.

When in general formula II Y represents a chlorine atom, the starting material is first cyclised to yield a dibenzo[a,d]cycloheptene derivative of the general formula:

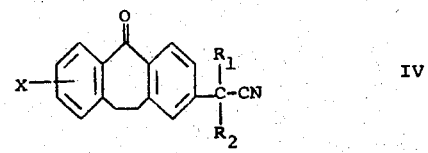
IV (wherein X, $R_1$ and $R_2$ are as hereinbefore defined) by means of a Friedel-Crafts reaction, and then the compound of general formula IV obtained is hydrolysed to convert the cyano radical to the carbamoyl (—$CONH_2$) radical and yield a dibenzo[a,d]cycloheptene derivative of general formula I wherein $R_3$ represents the amino (—$NH_2$) radical.

The Friedel-Crafts reaction is carried out, for example, by means of aluminium chloride in a solvent such as carbon disulphide, methylene chloride or nitrobenzene, or by means of antimony pentafluoride in nitromethane or nitrobenzene, working at approximately +5°C.

Hydrolysis of the intermediate product of general formula IV to yield a dibenzo[a,d]cycloheptene derivative of general formula I wherein $R_3$ represents the amino group may be carried out by heating the intermediate product in polyphosphoric acid, preferably at a temperature of about 80°–100°C.

According to another feature of the invention, the dibenzo[a,d]cycloheptene derivatives of general formula I, wherein $R_3$ represents a hydroxy radical, are prepared by the process which comprises the hydrolysis of a compound of the general formula:

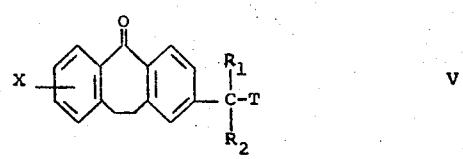
V wherein X, $R_1$ and $R_2$ are as hereinbefore defined, and T represents the cyano or carbamoyl radical, i.e. by hydrolysis of a compound of general formula III or IV by methods known per se for converting the cyano or carbamoyl radical to a carboxy radical.

The hydrolysis is generally carried out by heating the compound of formula V in an aqueous solution of a strong inorganic acid, for example sulphuric acid, preferably at a temperature of about 100°C.

According to another feature of the invention, the dibenzo[a,d]cycloheptene derivatives of general formula I, wherein $R_3$ represents an alkoxy radical containing 1 to 4 carbon atoms, a 4-(2,2-dimethyl-1,3-dioxolanyl)-methoxy radical or a group —$NR_4R_5$ in which $R_4$ and $R_5$ are as hereinbefore defined, are prepared by the process which comprises reacting a compound of the general formula:

$R_3 - H$     VI (wherein $R_3$ is as defined above in relation to general formula I with the exclusion of the hydroxy radical) with an acid halide of the generl formula:

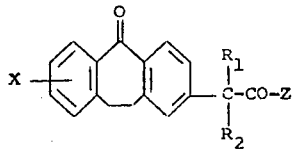
VII wherein X, $R_1$ and $R_2$ are as hereinbefore defined, and Z represents a halogen (preferably chlorine) atom. The reaction is generally carried out in an organic solvent such as methylene chloride at a temperature of from −10° to +50°C. When $R_3$ represents an alkoxy radical or a 4-(2,2-dimethyl-1,3-dioxolanyl)-methoxy radical, it is preferable to work in the presence of a basic condensation agent such as pyridine.

The compounds of general formula II wherein Y represents a hydroxy radical can be obtained by reacting a nitrile of the general formula:

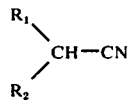
VIII (wherein $R_1$ and $R_2$ are as hereinbefore defined) with a benzoic acid derivative of the general formula:

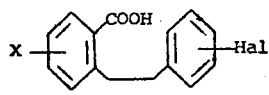
IX (wherein X is as hereinbefore defined, and Hal represents a chlorine or bromine atom in the 2- or 4-position) in accordance with the method of E. R. Biehl, J. Org. Chem., 31, 602 (1966). The reaction is generally carried out in anhydrous liquid ammonia in the presence of sodamide and at a temperature of about −30°C.

From the resulting compounds of general formula II (Y represents the hydroxy radical) there may be obtained corresponding compounds wherein Y represents a chlorine atom by methods known per se for the preparation of acid chlorides from acids, for example by reaction of the acids with thionyl chloride.

The reaction of a nitrile of the general formula VIII with a benzoic acid derivative of general formula IX can lead to a mixture of the compound of general formula II with its isomers, and particularly with a compound of the general formula:

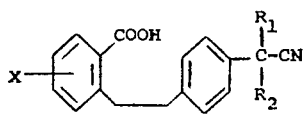
X wherein X, $R_1$ and $R_2$ are as hereinbefore defined. The compounds of general formula II can be isolated from these mixtures by applying the usual methods for the separation of constituents of such mixtures, and particularly by crystallisation or chromatography.

The benzoic acid derivatives of general formula IX can be obtained by reacting 2- or 4-chloro- or 2- or 4-bromo-phenylacetic acid with an anhydride of the general formula:

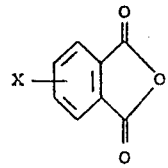
XI (wherein X is as hereinbefore defined), followed by reduction and hydrolysis of the product obtained.

The acid halides of the general formula VII can be obtained from dibenzo[a,d]cycloheptene-alkanoic acids conforming to general formula I, wherein $R_3$ represents a hydroxy radical, in accordance with the usual methods for the preparation of acid halides. For example, by reaction of thionyl chloride with the acid, preferably at the boiling point of the reaction mixture.

The new compounds of general formula I wherein $R_3$ represents a hydroxy radical can be converted into metal salts or addition salts with nitrogenous bases by application of methods known per se. Thus, these salts can be prepared by the action of an alkali metal or alkaline earth metal base, ammonia or an amine, on an acid of general formula I in a suitable solvent such as an alcohol, an ether, a ketone or water; the salt formed is precipitated, if necessary after concentration of the solution, and is separated by filtration or decantation.

When the meaning of $R_3$ as a group $-NR_4R_5$ ($R_4$ and $R_5$ being as hereinbefore defined) make this possible, the compounds of general formula I can also be converted into acid addition salts e.g. hydrochlorides.

The new dibenzo[a,d]cycloheptene derivatives of general formula I and their salts possess particularly valuable pharmacological properties; they are powerful analgesic, antipyretic and anti-inflammatory agents.

In rats, the compounds of general formula I and their salts have proved to be active when administered orally at doses of between 0.1 and 50 mg./kg. animal body weight, particularly in the following tests:

i. suppression of the pain phenomenon caused by mechanical compression at the site of an inflamed tissue in accordance with the technique of L. O. Randall and J. J. Selitto [Arch. Int. Pharmacodyn., 111, 409 (1957)] modified by K. F. Swingle et al [Proc. Soc. Exp. Biol. Med., 137, 536 (1971)], ii. antipyretic activity in which hyperthermia has been induced by subcutaneous injection of brewers yeast in accordance with the technique of R. Domenjoz [Ann. N.Y. Acad. Sci., 86, 263 (1960)], and iii. anti-inflammatory activity in accordance with the technique of K. F. Benitz and L. M. Hall [Arch. Int. Pharmacodyn., 144, 185 (1963)].

Preferred compounds of general formula I are those wherein X represents a hydrogen atom, $R_1$ represents a hydrogen atom or a methyl or ethyl radical and $R_2$ represents a hydrogen atom.

The toxicity of the compounds to mice when administered orally is greater than 300 mg./kg. animal body weight.

For use in human or veterinary therapy, the dibenzo[a,d]cycloheptene derivatives of general formula I can be employed as such or, when appropriate, in the form of pharmaceutically-acceptable salts, i.e. salts which are non-toxic to the animal organism in therapeutic doses of the salts.

The following non-limitative Examples illustrate the invention.

EXAMPLE 1

2-[3-(2-Carboxyphenethyl)phenyl]propionitrile (26 g.) is added to polyphosphoric acid (135 g.) [prepared from orthophosphoric acid (d = 1.7; 430 g.) and phosphorus pentoxide (500 g.)] and the emulsion obtained is heated for 1 hour at 100°C. After cooling, the reaction mixture is taken up in water (200 cc.) and methylene chloride (200 cc.). The organic layer is decanted, washed with a saturated solution of sodium bicarbonate (2 × 100 cc.) and then with water (2 × 100 cc.) and is finally dried over anhydrous sodium sulphate (50 g.). After evaporation of the solvent under reduced pressure (20 mm.Hg) at 60°C., the oil obtained is taken up in ethyl acetate (80 cc.). The product which crystallises is filtered off to give 2-(5-oxo-10,11-dihydrodibenzo[a,d]cyclohepten-2-yl)propionamide (6 g.), melting at 175°C. After recrystallisation from ethanol, the product melts at 181°C.

2-[3-(2-Carboxyphenethyl)phenyl]propionitrile is prepared in the following way:

Propionitrile (286.5 g.) is added over the course of 40 minutes and with vigorous stirring to a suspension of sodamide (248 g.) [prepared from sodium (139.5 g.) and liquid ammonia (4 liters)] and then 4-(2-carboxyphenethyl)chlorobenzene (117 g.) is added over the course of 10 minutes. The ammonia is allowed to evaporate during a period of 16 hours. The brown residue is taken up in anaesthetic grade diethyl ether (1 liter) and then in water (2 liters) with care. The alkaline aqueous solution is decanted, extracted with diethyl ether (2 × 400 cc.) and then acidified by adding sulphuric acid (d = 1.36; 350 cc.) whilst cooling. The oil which separates out is extracted with methylene chloride (2 × 500 cc.). The organic extracts are dried over anhydrous sodium sulphate (100 g.) and concentrated to dryness under reduced pressure (20 mm.Hg) at 60°C. The residual oil is dissolved in hot diisopropyl ether (120 cc.); on cooling, a product crystallises and is filtered off. 2-[4-(2-Carboxyphenethyl)phenyl]propionitrile (55 g.), melting at 73°C., is thus obtained; after three recrystallisations from ethyl acetate, the product melts at 129°C.

On concentrating the di-isopropyl ether mother liquors of the above product under reduced pressure (20 mm.Hg) at 60°C., an oil (62 g.) is obtained, the major portion of which consists of 2-[3-(2-carboxyphenethyl)phenyl]propionitrile.

EXAMPLE 2

3-(2-Carboxyphenethyl)phenylacetonitrile (2 g.) is added to polyphosphoric acid (20 g.) [prepared from orthophosphoric acid (d = 1.7; 1,120 g.) and phosphorus pentoxide (1,300 g.)], and the mixture is heated for 2 hours at 100°C. After cooling, the reaction mixture is poured into water (250 cc.); the oil which separates out is extracted twice with methylene chloride (total 150 cc.). The combined organic extracts are washed and dried over anhydrous sodium sulphate (10 g.) and the solvent is evaporated under reduced pressure (20 mm.Hg) at 60°C. to give (5-oxo-10,11-dihydrodibenzo[a,d]cyclohepten-2-yl)acetamide (1.8 g.) melting at 174°C. After recrystallisation from ethanol, the product melts at 185°C.

3-(2-Carboxyphenethyl)phenylacetonitrile is prepared in the following way:

Acetonitrile (128 g.) is added with vigorous stirring and over the course of 35 minutes to a suspension of sodamide (146 g.) [prepared from sodium (84 g.) and ammonia (4 liters)], and then 4-(2-carboxyphenethyl)chlorobenzene (70 g.) is added over the course of 10 minutes. The ammonia is allowed to evaporate for 16 hours. The reaction mixture is carefully taken up in water (2 liters) and diethyl ether (500 cc.). The alkaline aqueous solution is decanted, extracted twice with diethyl ether (total 1,000 cc.), and then acidified by adding concentrated sulphuric acid (d = 1.83, 150 cc.) whilst cooling. The oil which separates out is extracted three times with methylene chloride (total 1,500 cc.). The combined organic extracts are washed and dried over anhydrous sodium sulphate (200 g.) and the solvent is evaporated under reduced pressure (20 mm.Hg) at 60°C.

A mixture (81.6 g.) of 3-(2-carboxyphenethyl)phenylacetonitrile and 4-(2-carboxyphenethyl)phenylacetonitrile in about equal proportions is thus obtained. This mixture (36 g.) is taken up in boiling ethyl acetate (45 cc.). The product which crystallises on cooling is isolated. 3-(2-Carboxyphenethyl)phenylacetonitrile (12 g.), melting at 113°–120°C., is thus obtained. After two successive recrystallisations from ethyl acetate, the product melts at 130°C.

EXAMPLE 3

A suspension of 2-(5-oxo-10,11-dihydrodibenzo[a,d]cyclohepten-2-yl)propionamide (15 g.) in a mixture of sulphuric acid (d = 1.36; 50 cc.) and water (60 cc.) is heated with vigorous stirring for 3 hours at 110°C. After cooling, the product which precipitates is filtered off and then added to N sodium hydroxide solution (55 cc.). The alkaline solution, clarified by filtration, is acidified acid adding N hydrochloric cid (60 cc.). The product which precipitates is filtered off, dried and then recrystallised from carbon tetrachloride (170 cc.) to give 2-(5-oxo-10,11-dihydrodibenzo[a,d]cyclohepten-2-yl)propionic acid (7.4 g.) melting at 122°C.

EXAMPLE 4

A suspension of (5-oxo-10,11-dihydrodibenzo[a,d]cyclohepten-2-yl)acetamide (17.4 g.) in a mixture of concentrated sulphuric acid (d = 1.83; 70 cc.) and water (70 cc.) is heated with vigorous stirring for 3 hours at 100°C. After cooling, the product which precipitates is filtered off and then added to 2N sodium hydroxide solution (200 cc.). The alkaline solution is extracted with diethyl ether and then acidified by adding 2N sulphuric acid (250 cc.). The product which precipitates is filtered off, dried and then recrystallised from ethyl acetate (100 cc.) to give (5-oxo-10,11-dihydrodibenzo[a,d]cyclohepten-2-yl)acetic acid (11.5 g.) melting at 154°C.

EXAMPLE 5

Following the procedure of Example 4 but starting with 2-(5-oxo-10,11-dihydrodibenzo[a,d]cyclohepten-2-yl)butyramide (11.8 g.), 2-(5-oxo-10,11-dihydrodibenzo[a,d]cyclohepten-2-yl)butyric acid (7.35 g.), melting at 125°C., is obtained.

EXAMPLE 6

A 2.6N solution of methylamine in methylene chloride (250 cc.) is added at 0°C. and over the course of 30 minutes to a solution of 2-(5-oxo-10,11-dihydrodibenzo[a,d]cyclohepten-2-yl)propionyl chloride (10 g.) in methylene chloride (100 cc.). The reaction mixture is concentrated, and the residue taken up in distilled water (100 cc.) and benzene (300 cc.). The organic layer is decanted, dried over anhydrous sodium sulphate and evaporated at 60°C. under reduced pressure (20 mm.Hg). The product obtained is recrystallised from di-isopropyl ether (100 cc.) to give 2-(5-oxo-10,11-dihydrodibenzo[a,d]cyclohepten-2-yl)-N-methylpropionamide (5.8 g.) melting at 140°C.

2-(5-Oxo-10,11-dihydrodibenzo[a,d]cyclohepten-2-yl)propionyl chloride is obtained by heating 2-(5-oxo-10,11-dihydrodibenzo[a,d]cyclohepten-2-yl)propionic acid (28 g.) in thionyl chloride (280 cc.) for 1 hour. After cooling, the thionyl chloride is evaporated at 60°C. under reduced pressure (20 mm.Hg). 2-(5-Oxo-10,11-dihydrodibenzo[a,d]cyclohepten-2-yl)propionyl chloride (28.8 g.) is thus obtained in the form of an oil.

Following the same procedure but replacing the methylamine with isopropylamine, 2-(5-oxo-10,11-dihydrodibenzo[a,d]cyclohepten-2-yl)-N-isopropylpropionamide, melting at 142°C., is obtained.

EXAMPLE 7

Following the procedure of Example 6 but starting with 2-(5-oxo-10,11-dihydrodibenzo[a,d]cyclohepten-2-yl)propionyl chloride (10 g.) and dimethylamine (4.5 g.), 2-(5-oxo-10,11-dihydrodibenzo[a,d]cyclohepten-2-yl)-N,N-dimethylpropionamide (10 g.) is obtained in the form of an oil.

Rf = 0.55 (silica; chloroform - ethyl acetate: 80–20 by volume).

EXAMPLE 8

Following the procedure of Example 6 but starting with 2-(5-oxo-10,11-dihydrodibenzo[a,d]cyclohepten-2-yl)propionyl chloride (8 g.) and aniline (7.5 g.), 2-(5-oxo-10,11-dihydrodibenzo[a,d]cyclohepten-2-yl)-N-phenylpropionamide (6.7 g.), melting at 149°C., is obtained after recrystallisation from isopropanol (100 cc.).

EXAMPLE 9

Following the procedure of Example 6 but starting with 2-(5-oxo-10,11-dihydrodibenzo[a,d]cyclohepten-2-yl)propionyl chloride (8 g.) and 1-methylpiperazine (8.2 g.), 4-[2-(5-oxo-10,11-dihydrodibenzo[a,d]cyclohepten-2-yl)propionyl]-1-methylpiperazine (10 g.) is obtained in the form of an oil.

This oil is dissolved in diethyl ether (100 cc.), and a 3.1N solution of hydrogen chloride in diethyl ether (8.5 cc.) is added. The product which crystallises is filtered off and recrystallised from acetone (10 cc.) to give 4-[2-(5-oxo-10,11-dihydrodibenzo[a,d]cyclohepten-2-yl)propionyl]-1-methylpiperazine hydrochloride (4.3 g.) melting at 216°C.

EXAMPLE 10

Following the procedure of Example 6 but starting with 2-(5-oxo-10,11-dihydrodibenzo[a,d]cyclohepten-2-yl)propionyl chloride (1 g.) and 2-aminoethanol (2 g.), 2-(5-oxo-10,11-dihydrodibenzo[a,d]cyclohepten-2-yl)-N-2-hydroxyethyl-propionamide (11 g.), melting at 118°C., is obtained.

EXAMPLE 11

A solution of 2-(5-oxo-10,11-dihydrodibenzo[a,d]cyclohepten-2-yl)propionyl chloride (10 g.) in methylene chloride (100 cc.) is added at 20°C. and over the course of 10 minutes to a mixture of methanol (100 cc.) and anhydrous pyridine (10 cc.). On concentrating the reaction mixture to dryness, a paste-like residue (weighing 14 g.) is obtained and the latter is taken up in diethyl ether (500 c.) and water (100 cc.). The ether phase is decanted, washed twice with water (total 100 cc.) and dried over potassium carbonate. On concentrating to dryness, methyl 2-(5-oxo-10,11-dihydrodibenzo[a,d]cyclohepten-2-yl)propionate (8.6 g.) is obtained.

Rf = 0.83 (silica; ethyl acetate).

EXAMPLE 12

Following the procedure of Example 11 but starting with 2,2-dimethyl-4-hydroxymethyl-1,3-dioxolane (0.5 g.), anhydrous pyridine (0.6 cc.) and 2-(5-oxo-10,11-dihydrodibenzo[a,d]cyclohepten-2-yl)propionyl chloride (1 g.), a residue (1 g.) is obtained after concentrating the reaction mixture. This residue is taken up in chloroform (20 cc.), and the resulting solution chromatographed on a column of height 17 cm. containing silica (10 g.). Elution is carried out with chloroform, and fractions (10 cc.) of eluate are collected. The first two fractions of eluate are combined and, after concentrating to dryness, 4-[2-(5-oxo-10,11-dihydrodibenzo[a,d]cyclohepten-2-yl)propionyloxymethyl]-2,2-dimethyl-1,3-dioxolane, form A (0.2 g.), melting at 80°C., is obtained.

The third fraction of eluate (10 cc.) gives, after concentration to dryness, 4-[2-(5-oxo-10,11-dihydrodibenzo[a,d]cyclohepten-2-yl)propionyloxymethyl]-2,2-dimethyl-1,3-dioxolane, form B (0.2 g.), in the form of an oil.

Rf = 0.84 (silica; chloroform - ethyl acetate: 80–20 by volume).

The present invention includes within its scope pharmaceutical compositions which comprise, as active ingredient, at least one dibenzo[a,d]cycloheptene derivative of general formula I, or when appropriate a pharmaceutically-acceptable salt thereof, in association with a pharmaceutical carrier or coating. The invention includes especially such compositions made up for oral, rectal or parenteral administration.

Solid compositions for oral administration include tablets, pills, powders or granules. In such solid compositions, the active compound is admixed with at least one inert diluent such as sucrose, lactose or starch. The compositions may also comprise, as is normal practice, additional substances other than inert diluents, e.g. lubricating agents such as magnesium stearate. Liquid compositions for oral administration include pharmaceutically-acceptable emulsions, solutions, suspensions, syrups and elixirs containing inert diluents commonly used in the art such as water or liquid paraffin. Besides inert diluents such compositions may also comprise adjuvants, such as wetting, emulsifying and suspending agents, and sweetening, flavouring and aromatizing agents. Compositions according to the invention for oral administration also include capsules of absorbable material such as gelatin containing the active substance with or without the addition of diluents or excipients.

Compositions according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. The compositions may also contain adjuvants, such as wetting, emulsifying and dispersing agents. They may be sterilised by, for example, filtration through a bacteria-retaining filter, by incorporation in the compositions of sterilising agents, by irradiation or by heating. They may also be manufactured in the form of sterile solid compositions which can be dissolved in sterile water or some other sterile injectable medium immediately before use.

Compositions for rectal administration are suppositories which contain, in addition to the active substance, excipients such as cacao butter or a suppository wax.

The percentage of active ingredient in compositions of the invention may be varied, it being necessary that it should constitute a proportion such that a suitable dosage shall be obtained. In human therapy, the dosages depend on the desired therapeutic effect, on the route of administration and on the duration of the treatment; they are generally between 50 and 1,000 mg. per day when administered orally to an adult.

The compositions according to the invention are particularly useful as analgesic agents. They can be used in the treatment of acute or chronic algias of rheumatic or dental origin or the like.

In every case, the doctor will decide the most suitable posology, taking into account the age, weight and all other factors relating to the patient to be treated.

The following Examples illustrate pharmaceutical compositions according to the invention.

EXAMPLE 13

Tablets containing 250 mg. of active substance and having the following composition are prepared in accordance with the usual technique:

| | |
|---|---|
| 2-(5-oxo-10,11-dihydrodibenzo[a,d]-cyclohepten-2-yl)propionic acid | 250 mg. |
| starch | 190 mg. |
| colloidal silica | 50 mg. |
| magnesium stearate | 10 mg. |

EXAMPLE 14

Tablets containing 250 mg. of active substance and having the following composition are prepared in accordance with the usual technique:

| | |
|---|---|
| 2-(5-oxo-10,11-dihydrodibenzo[a,d]-cyclohepten-2-yl)propionamide | 250 mg. |
| starch | 190 mg. |
| colloidal silica | 50 mg. |
| magnesium stearate | 10 mg. |

EXAMPLE 15

Tablets containing 250 mg. of active substance and having the following composition are prepared in accordance with the usual technique:

| | |
|---|---|
| 2-(5-oxo-10,11-dihydrodibenzo[a,d]-cyclohepten-2-yl)-N-methylpropionamide | 250 mg. |
| starch | 190 mg. |
| colloidal silica | 50 mg. |
| magnesium stearate | 10 mg. |

We claim:

1. A dibenzo[a,d]cycloheptene of the formula:

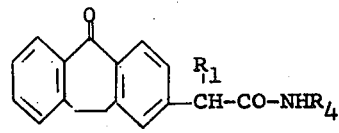

wherein $R_1$ is hydrogen or methyl, and $R_4$ is hydrogen, methyl or phenyl.

2. A dibenzo[a,d]cycloheptene compound according to claim 1 which is 2-(5-oxo-10,11-dihydrodibenzo[a,d]cyclohepten-2-yl)propionamide.

3. A dibenzo[a,d]cycloheptene compound according to claim 1 which is (5-oxo-10,11-dihydrodibenzo[a,d]cyclohepten-2-yl)acetamide.

4. A dibenzo[a,d]cycloheptene compound according to claim 1 which is 2-(5-oxo-10,11-dihydrodibenzo[a,d]cyclohepten-2-yl)-N-methylpropionamide.

5. A dibenzo[a,d]cycloheptene compound according to claim 1 which is 2-(5-oxo-10,11-dihydrodibenzo[a,d]cyclohepten-2-yl)-N-phenylpropionamide.

* * * * *

UNITED STATES PATENT OFFICE
CERTIFICATE OF CORRECTION

Patent No. 3,975,437   Dated August 17, 1976

Inventor(s) Jean-Paul BRUNET et al

It is certified that error appears in the above-identified patent and that said Letters Patent are hereby corrected as shown below:

Under "[30] Foreign Application Priority Data", the date of the second priority application should be changed from "73.17404" to --73.37404--.

Signed and Sealed this

Fourth Day of January 1977

[SEAL]

Attest:

RUTH C. MASON
*Attesting Officer*

C. MARSHALL DANN
*Commissioner of Patents and Trademarks*